US008128683B2

(12) United States Patent
Lippoth et al.

(10) Patent No.: US 8,128,683 B2
(45) Date of Patent: Mar. 6, 2012

(54) LONGITUDINALLY FLEXIBLE TEXTILE VASCULAR PROSTHESIS

(75) Inventors: Lisa Lippoth, Denkingen (DE); Christof Merckle, Mannheim (DE); Helmut Goldmann, Tuttlingen (DE); Jürgen Scherberich, Kempen (DE); Hans-Hinrich Sievers, Kronshagen (DE)

(73) Assignees: Aesculap & Co. KG, Tuttlingen/Donau (DE); Hans-Hinrich Sievers, Kronshagen (DE)

( * ) Notice: Subject to any disclaimer, the term of this patent is extended or adjusted under 35 U.S.C. 154(b) by 994 days.

(21) Appl. No.: 11/632,899

(22) PCT Filed: Jul. 20, 2005

(86) PCT No.: PCT/EP2005/007907
§ 371 (c)(1),
(2), (4) Date: Nov. 14, 2007

(87) PCT Pub. No.: WO2006/008148
PCT Pub. Date: Jan. 26, 2006

(65) Prior Publication Data
US 2008/0065199 A1    Mar. 13, 2008

(30) Foreign Application Priority Data

Jul. 21, 2004  (DE) .......................... 10 2004 035 272
Aug. 12, 2004  (DE) .......................... 10 2004 039 980

(51) Int. Cl.
*A61F 2/82*    (2006.01)

(52) U.S. Cl. ........................ 623/1.28; 623/1.29; 623/1.1

(58) Field of Classification Search ................. 623/1.28, 623/1.29; A61F 02/06
See application file for complete search history.

(56) References Cited

U.S. PATENT DOCUMENTS

| 2,836,181 | A | 5/1958 | Tapp |
| 4,169,422 | A | 10/1979 | Hayes et al. |
| 4,544,599 | A | 10/1985 | Buttazzoni |
| 4,730,566 | A | 3/1988 | Brophy et al. |
| 2003/0088305 | A1 | 5/2003 | Van Schie et al. |

FOREIGN PATENT DOCUMENTS

| DE | 41 28 611 | 3/1992 |
| DE | 199 21 017 C1 | 1/2001 |
| DE | 101 62 821 | 6/2003 |
| DE | 102 42 153 | 3/2004 |

(Continued)

OTHER PUBLICATIONS

Office Action issued by the German Patent Office, for corresponding priority German Application DE 10 2004 035 272.0, dated Jun. 30, 2005.

(Continued)

*Primary Examiner* — Thomas J Sweet
*Assistant Examiner* — Jason-Dennis Stewart
(74) *Attorney, Agent, or Firm* — The Nath Law Group; Jerald L. Meyer; Jiaxiao Zhang

(57) ABSTRACT

The invention relates to a textile vascular prosthesis (1) with a circulatory pleating formed by folds (4), and with an arch-shaped longitudinal flexion (2) extending over at least a partial section and formed by asymmetric shortening gathering of the prosthesis wall by means of at least one longitudinal seam (7) extending along the partial section. The at least one longitudinal seam gathers the prosthesis wall while preserving the accordion-like structure (4) and the compacted state of the pleating (4) in the longitudinal direction.

13 Claims, 3 Drawing Sheets

FOREIGN PATENT DOCUMENTS

Figure 1:
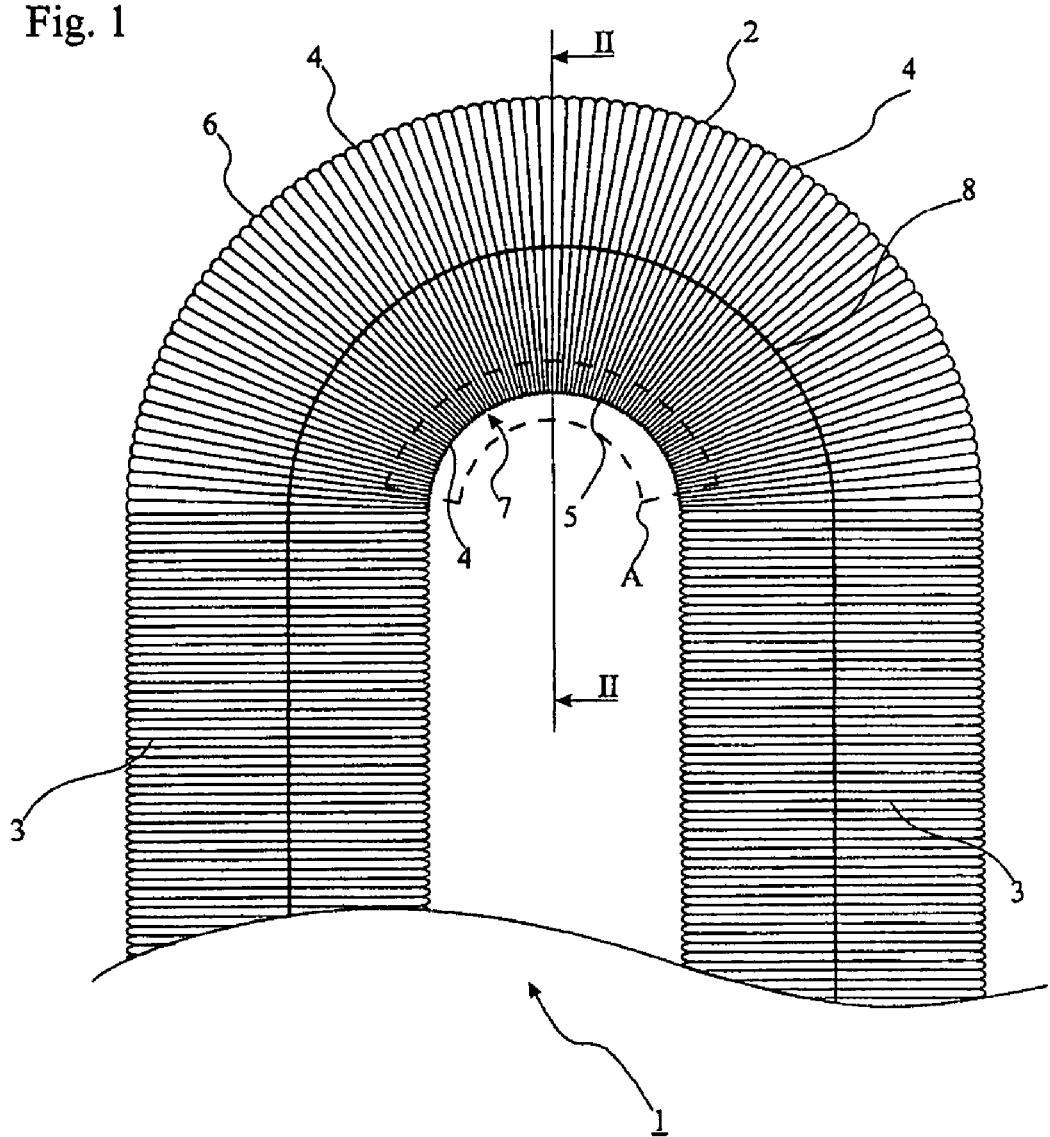

| | | |
|---|---|---|
| DE | 103 28 175 | 12/2004 |
| EP | 0 251 331 | 1/1988 |
| EP | 0 306 690 | 9/1993 |
| EP | 1 371 345 | 4/1995 |
| EP | 1 178 144 | 2/2002 |
| WO | 00/47271 | 8/2000 |
| WO | 03/034948 | 5/2003 |
| WO | 03/051232 | 6/2003 |

OTHER PUBLICATIONS

Extended European Search Report issued by the European Patent Office, for parallel European Patent Application EP 11 16 9560, dated Aug. 4, 2011.

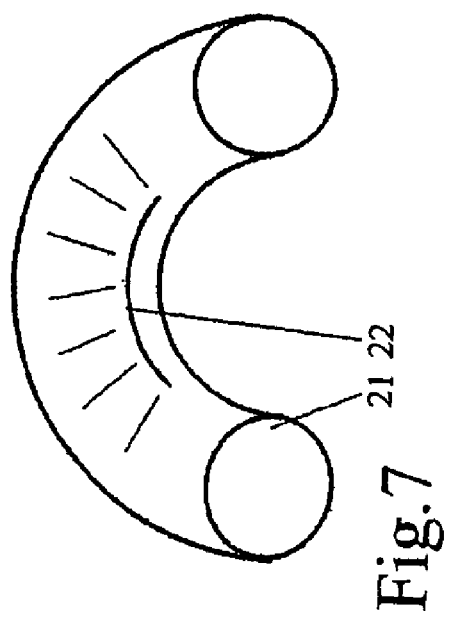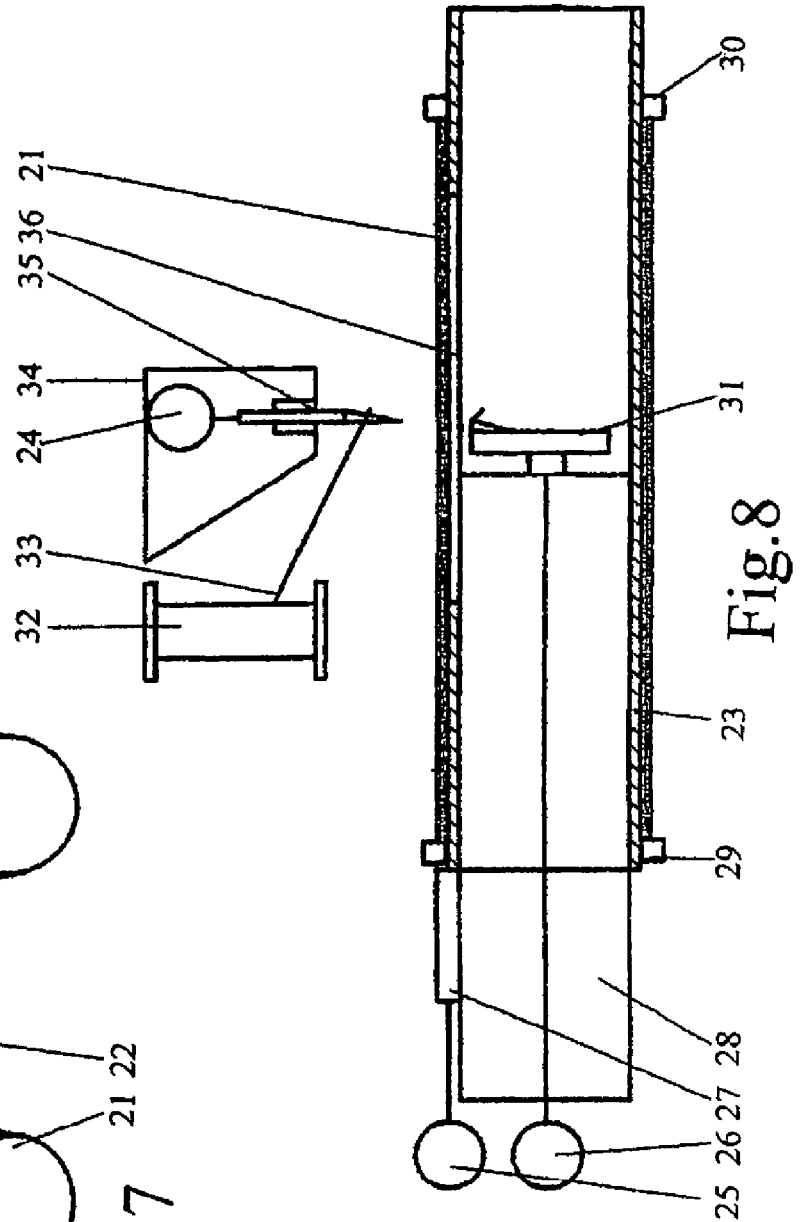

LONGITUDINALLY FLEXIBLE TEXTILE VASCULAR PROSTHESIS

The invention relates to a textile vascular prosthesis with a circulatory pleating formed by folds, and with an arch-shaped longitudinal flexion extending over at least a partial section and formed by asymmetric shortening gathering of the prosthesis wall by means of at least one longitudinal seam extending along the partial section. The prosthesis according to the invention serves in particular for replacement of the aortic arch and parts of the ascending and descending aorta.

WO 03/034948 A1 discloses a pleated vascular prosthesis in which an arch shape is stabilized by means of in each case two adjacent fold peaks of the pleating being sewn together by transversely extending seams, these transversely extending seams extending approximately across half the diameter of the vascular prosthesis in the transverse direction. It is also known from said document to stabilize the arch shape of prostheses by means of stents introduced in the area of the arch. In WO 03/051232, various combinations of longitudinal and/or transverse seams are described for stabilizing the arch of vascular prostheses. The results are satisfactory. However, a simpler production method is desired, in particular a machine-based stabilization of the arch.

In a not previously published, older patent application DE 103 28 175.4, it is proposed, among other things, for the folds of the pleating to be pressed together in the radial or tangential direction so as to be able to easily produce machine seams. In doing so, account is taken of a deformation of the vascular prosthesis in cross section.

The object of the invention is to provide a simple way of stabilizing the arch of vascular prostheses, in particular one that also permits simple machine production with improved results.

The invention is characterized in that the at least one longitudinal seam gathers the prosthesis wall while preserving the accordion-like structure and the compacted state of the pleating in the longitudinal direction.

The invention affords numerous advantages. On the one hand, an effective configuration of the arch is achieved by the compaction of the pleating and by the associated tight juxtaposition of the individual folds of the pleating. On the other hand, the tightly contiguous folds of the pleating mutually support one another, so that the arrangement of a seam whose stitches pass radially through the compacted prosthesis wall are formed in a simple manner, without the structure of the pleating being lost, i.e. the pleating being pressed together in the radial direction. By means of the compaction, the seam can also be made strong and thus designed with tensile strength. The thread or threads of the at least one seam can loop round the folds of the compacted accordion-like structure, as a result of which the compacted state can be particularly effectively maintained.

The vascular prosthesis can be woven or knitted in the usual manner. The pleating can be formed with closed rings or can also have a helical formation. The fold depth of the pleating is generally 0.5 to 2.5 mm, preferably 1 to 1.5 mm. There are generally 3 to 12, in particular 4 to 8 folds per cm of prosthesis length in the relaxed, non-compacted state (straight section). The arch shape of the vascular prosthesis can be preformed by thermal fixing, which proves to have a favorable effect.

In a preferred embodiment, the gathering is effected exclusively by the at least one longitudinal seam, if appropriate supported by the thermal prefixing. No transverse seams are provided, and no other devices such as lattices or stents supporting the arch shape.

In one embodiment of the invention, the at least one longitudinal seam is formed from at least one continuous thread. This design permits particularly simple production. As has already been mentioned, the at least one seam is advantageously formed as a machine seam. It can be produced in particular with the aid of a long-arm sewing machine. In a preferred embodiment of the invention, the at least one seam is formed on a vascular prosthesis which is compacted by compression and in which the folds of the pleating lie close together, and the seam secures the vascular prosthesis in this state on the inside of the arch. On the outside of the arch, which is free of a seam, the pleating is opened again to form the arch.

The seam can be formed by a single thread or two threads. If the seam is formed with a single-thread system, a single-chain stitch is suitable for this purpose. If the seam is designed as a two-thread system, then a double-chain stitch is suitable. A lock stitch can also be provided for forming the seam.

There are seams that are not automatically secure against unraveling. At least in such cases, one or both thread ends are secured against undesired unraveling of the seam. It can also be advantageous, in particular in such seams, to provide intermediate securing. Arch sections can then be portioned off without risk of unraveling. The securing of the thread ends, and preferably also the intermediate securing between the thread ends, can be carried out by machine. It is also possible to provide intermediate securing by hand, for example by overstitching the machine seam, e.g. with cross stitches. This can be done in particular during final inspection of the finished arches, when any mesh widening in the area of the seam is closed, particularly with velour threads.

In certain embodiments, several seams, in particular 2 to 4 seams, can extend parallel and alongside one another in the longitudinal direction. This can be of advantage especially in aortic arches of large diameter. The distance between the parallel longitudinal seams can advantageously be in the range of 1 to 15 mm, in particular 1 to 3 mm, and distances of over 10 mm to 15 mm are generally possible only in the case of two eccentric longitudinal seams. It is also possible to provide partial seams which supplement one another. Thus, several parallel partial seams that preferably overlap can extend in the longitudinal direction. This can be advantageous if partial sections are cut off from a larger arch. Several partial seams can also be arranged behind one another in the longitudinal direction, with intervals between them. This affords the possibility of widening the arch, i.e. increasing the radius while at the same time maintaining the compacted state of the pleating in the seam area. The seam ends of the partial seams are also preferably secured against undesired loosening. The seam ends can be secured for example by seam compaction, sewing, knotting or tying. It is also advantageously possible to form several seams, in particular partial seams, with the same thread or same threads, without thread interruption. The intermediate seam-free sections of the prosthesis can then be bridged by the continuous thread. All the longitudinal seams are preferably arranged only in the area of the inside of the arch.

In preferred embodiments of the invention, the length of the gathered longitudinal area of the vascular prosthesis is at least 10 mm, in particular 20 to 70 mm, depending on the arch size and/or diameter of the vascular prosthesis. The arch size can be between 60° and 270°, in particular between 90° and 180°, and, if necessary, even greater. The clear diameter is generally 8 mm to 50 mm, and preferably in the upper range for aortic arches. The seam length of partial seams, in particular of partial seams arranged behind one another and/or offset alongside one another, is generally at least 5 mm, in particular in the range of 10 to 20 mm. The stitch length, in particular loop length, of the at least one seam is advantageously 1 to 3 mm, in particular ca 2 mm. For each stitch length or loop length of the seam, two to four closely contiguous pleating folds, in particular three pleating folds, can be enclosed, in particular completely. Since the stitches do not need to coincide exactly with the pleating folds, the number of pleating folds enclosed by a stitch length does not need to be an integer.

In preferred embodiments of the invention, the at least one longitudinal seam advantageously extends between two guidelines extending in the longitudinal direction of the vascular prosthesis. The guidelines can thus be easily seen on both sides of the arch.

The threads advantageously have a coloring that allows them to be clearly distinguished from the color of the textile base material of the vascular prosthesis. In this way, the course of the inside of the arch can also be recognized during the operation.

The threads used are preferably multifilament threads, in particular coated threads. Threads with a thread size of 1/0 to 5/0, preferably 2/0 to 4/0, can be used. In the case of asymmetric seams that have a different pattern on one side of the vessel wall than on the other side, it is advantageously possible to apply the at least one seam when the vascular prosthesis has been turned inside out, and then to turn it back again.

The invention also relates to a method for generating a deliberate and permanent curvature on an artificial vascular prosthesis. The method is characterized in that a vascular prosthesis, which optionally has a thermally prefixed arch, is axially compressed or compacted, and the seam is applied at the site or sites where elastic extension is to be prevented, after which the prosthesis is allowed to axially expand and form the arch shape. The invention further relates to a device for generating a deliberate and permanent curvature on an artificial vascular prosthesis, said device comprising a chain-stitch sewing machine with an arm that encloses the sewing needle drive for a sewing needle, with a reel holding a thread, whose end can be guided by the sewing needle, with a support for the material to be sewn, with a gripper that chain-stitches the thread after the material is pierced by the needle, and with a feed device for the material.

The invention also relates to an artificial vascular prosthesis which acquires a deliberate and permanent curvature by means of a sewing procedure.

The compressed prosthesis is preferably received by a support tube, on which the compression can also be performed.

The sewing procedure is made particularly easy by the fact that the vascular prosthesis is applied on a support tube and is compressed thereon. The vascular prosthesis is compressed very uniformly along its length. The support tube prevents bending of the vascular prosthesis during the sewing process. After the vascular prosthesis has been withdrawn from the support tube, the thread, which is sewn in in the axial direction into the wall of the elastic tube, prevents the vascular prosthesis from springing back on part of the circumference, namely in the area of the sewn area. On the opposite side of the seam, the vascular prosthesis will spring back with less obstruction. After it has been withdrawn from the support tube, the vascular prosthesis in this way automatically adopts an arch shape, the curvature of which is dependent on the original compression and the length of the seam.

It is advantageous if the support tube is moved in the axial direction during the sewing process. This permits a uniform seam.

It is advantageous to generate the seam by means of a sewing needle. In this case, the single chain stitch is possible and recommended.

The sewing needle preferably passes through the vascular prosthesis, and through an oblong hole or slit formed in the wall of the support tube, into the interior of the support tube. The thread can then be knotted inside the vascular prosthesis.

For the same reason it is advantageous if a thread gripper is arranged in the interior of the vascular prosthesis and in particular of the support tube and takes up the thread from the needle and chain-stitches it.

To increase the speed of the method, it is advisable to allow the thread gripper to rotate.

Safety is improved if, during its axial movement, the support tube encloses the rotating thread gripper. Injuries caused by handling the latter are thus avoided.

It is of particular advantage if, before being received on the support tube, the vascular prosthesis is turned inside out, that is to say the inside surface faces outward, and vice versa. This has the effect that the knotting made on the inside in the chain-stitch method is subsequently turned back outward again. The knots do not then impede the circulation of blood. The method applied in this way also permits more exact control of the seam and a better possibility of arranging the locks or knots at the start and end of the seam. For example, the shortening of the end threads can be effected much more precisely.

It is advantageous if the compression of the vascular prosthesis on the support tube is effected manually. This permits the simplest and quickest application of the method.

In work requiring absolute precision, or involving the same working procedures recurring several times, it may also be expedient to use a compression device for the compression.

For this purpose, it is advisable to support the vascular prosthesis at least on an adjustable end abutment. This ensures a possibility of exact adjustment and reproducibility of the procedure.

For the device for producing a deliberate and permanent curvature of a vascular prosthesis, it is advantageous if a support tube is present onto which the vascular prosthesis can be pushed in compressed form. This ensures a more secure hold for the subsequent sewing procedure.

The external diameter of the support tube preferably corresponds approximately to the internal diameter of the vascular prosthesis. The secure hold is assisted by this means.

It is advantageous if the support tube is connected to a feed device. The vascular prosthesis in compressed form is then guided with a firm fit on the support tube under the needle, which leads to a uniform seam structure.

Further advantageous embodiments of the device are described in the dependent claims.

The invention also relates to a curved elastic vascular prosthesis that has been produced by the stated measures in one of the method claims.

Figure 2:
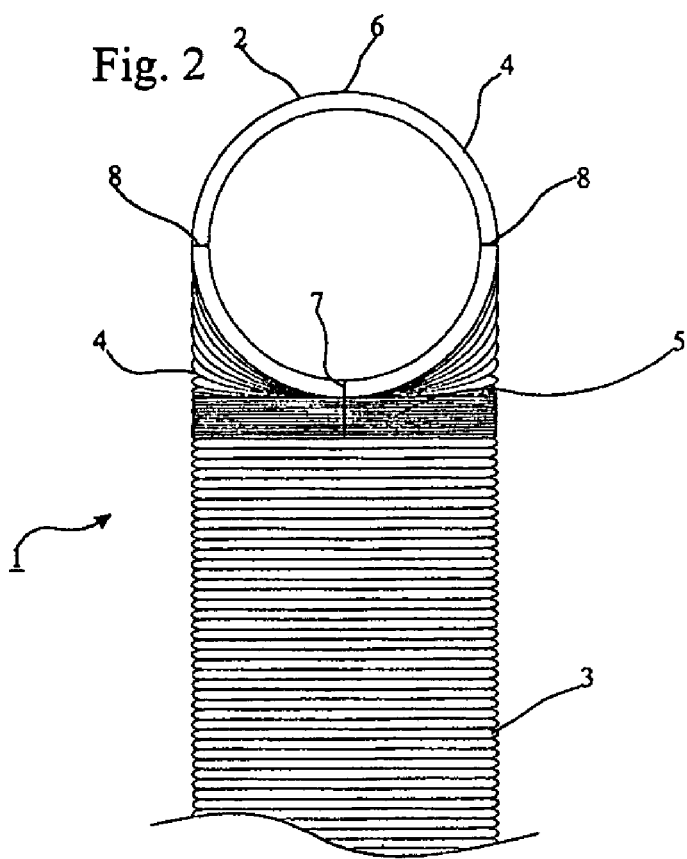
Figure 3:
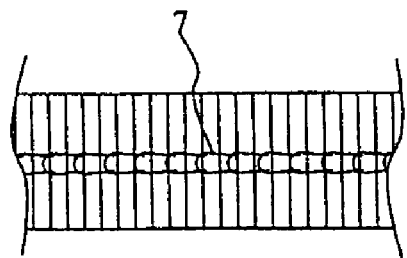
Figure 4:
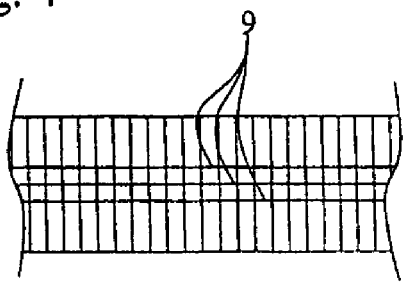
Figure 5:
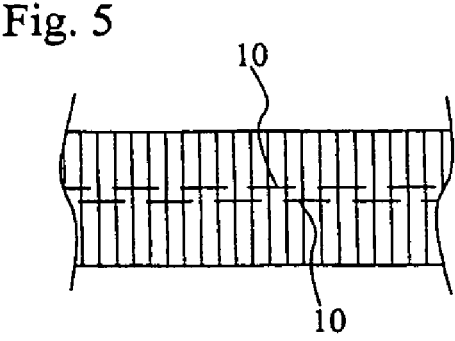
Figure 6:
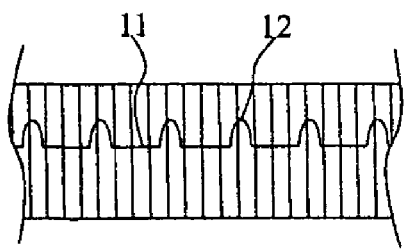

Further features and advantages of the invention will become clear from the following description of preferred embodiments in conjunction with the drawing and with the dependent claims. The individual features can be realized in isolation or in combination with one another. In the drawing:

FIG. 1 shows a side view of an embodiment of an aortic arch according to the invention, FIG. 2 shows a cross section along the line II-II in FIG. 1, FIG. 3 shows a schematic representation of the area A on the inside of the aortic arch according to FIG. 1, FIG. 4 shows a schematic representation of the area A in another embodiment, FIG. 5 shows a schematic representation of the area A in a further embodiment, FIG. 6 shows a schematic representation of the area A in a further embodiment, FIG. 7 shows a schematic and perspective representation of a vascular prosthesis produced according to the invention, FIG. 8 shows a schematic representation of a device according to the invention for producing the curved vascular prosthesis.

In the embodiment shown in FIGS. 1 and 2 of the drawing, an aortic arch 1 is provided which has an arch section 2 with a bend of 180°. The arch section is adjoined by straight end pieces 3 which are sewn onto the remaining parts of the natural aorta. The aortic arch 1 has an internal diameter of 33 mm and a pleating with seven folds 4 per cm. The fold depth is ca 1.5 mm. The folds 4 lie tight on one another on the inside 5 of the arch and widen continuously to the outside 6 of the arch. The compacted state of the folds on the inside 5 of the arch is stabilized by a single longitudinal seam 7. The stitches of the longitudinal seam pass through the compacted accordion structure on the inside of the arch in the radial direction and form contiguous loops that each enclose ca three folds. On both sides of the aortic arch there is a guideline 8, the two guidelines being designed with different widths. The sewing material of the longitudinal seam 7 has a coloring that can be distinguished clearly from the white base color of the aortic arch, even in the state saturated with blood.

The thread of the longitudinal seam 7 is a multi-filament silicone-coated thread of thread size 3/0. The seam is based on a single-thread system in which one thread is sewn in a single chain stitch (FIG. 3). In this system, a thread loop is guided radially through the prosthesis wall, transferred in the seam direction and, at the next stitch, caught by the next loop. A longitudinal chain of contiguous loops is thus formed. On the other side, the single thread is guided from stitch to stitch in the longitudinal direction.

To produce the longitudinal seam, a section of a knitted vascular prosthesis used to form the aortic arch and with a pleated or accordion structure is expediently pushed together as far as possible rectilinearly in the longitudinal direction on a support device, until the individual folds of the accordion structure in the compacted state lie parallel and closely alongside one another. In this state, the longitudinal seam is prepared for example with a long-arm sewing machine, the thread passing radially through the compacted folds. The thread ends are locked, by thread compaction, against undesired unraveling. Intermediate locking is also possible. When the compacted accordion structure is removed from the support device, the folds of the pleating relax again, except for the folds that are prevented from coming apart by the longitudinal seam on the inside of the arch. In this way, a uniform aortic arch is formed. The length of the longitudinal seam is ca 50 mm.

FIGS. 3 to 6 show different embodiments of longitudinal seams which without exception are located on the inside of the arch. FIG. 3 shows the single longitudinal seam 7 of the embodiment according to FIG. 1. In the embodiment according to FIG. 4, three parallel longitudinal seams 9 are provided which are at a distance of 1 to 2 mm from one another. FIG. 5 shows partial longitudinal seams 10 which are arranged in two rows at a distance of 2 mm and mutually offset from one another. The partial longitudinal seams have a length of ca 10 mm. The thread ends are each secured against unraveling. FIG. 6 shows partial longitudinal seams 11 which extend in a line and each have interruptions 12 between them. The interruptions 12 have the result that the accordion structure is not compacted in the area thereof, i.e. expands again after the seam has been formed. By means of such interruptions it is possible to control the size of the arch width and of the arch radius. By suitable control of the seam, the partial longitudinal seams 11 and/or the interruptions 12 between them can also have different sizes, as a result of which it is possible to obtain arch forms that differ from the circular ach form. If, in the case of seams having a different pattern on one side than on the other, it is desired to have a certain seam side to the outside, this can be achieved if the prosthesis, before the compression and before the formation of the seam, is turned inside out and then turned back out again.

By virtue of the compacted areas of the accordion structure being held together on the inside of the arch, a uniform arch shape is obtained. The circular inner cross section of the aortic arch is maintained despite the machine production of the seam, in which a certain contact pressure is required.

The aortic arch according to the invention can be impregnated in the usual manner and packed in a sterile form. If the whole length of the arch is not used, an appropriate arch section can be cut off prior to the operation. Preference is given here to aortic arches with seams that have intermediate locking of the threads, or partial threads with end locking.

Machine production can also be made easier if several seams, for example parallel seams or partial seams, are sewn with a continuous thread, which then bridges the gap areas, as is shown schematically in FIG. 6.

FIG. 7 shows an elastic vascular prosthesis produced according to the invention. It is made of a biocompatible and durable material, for example polyethylene terephthalate. The order of size of the diameters varies within the two-digit millimeter range, preferably in the range of 20 to 40 mm. During the production of the curvature, the vascular prosthesis is compressed by being pushed onto a support tube 23 and provided with at least one seam 22 extending at least over part of the length of the wall. After the vascular prosthesis 21 has been withdrawn from the support tube 23 and after release of the elastic compression, this ensures that the compression is maintained in the area of the seam 22. As the distance from the seam 22 increases on the circumference of the vascular prosthesis 21, the wall relaxes more noticeably and can expand elastically again. This automatically leads to a bending of the vascular prosthesis 21. The seam 22 is generated with a biocompatible thread 33, for example of polyethylene terephthalate. It is sometimes advantageous to turn the vascular prosthesis 21 around before it is applied in the compressed state onto the support tube 23, that is to say to turn the outer side inward and vice versa. If the vascular prosthesis 21 is turned back again when finished, the knots are then on the outside and do not disturb the circulation of blood.

FIG. 8 is a simplified representation of a suitable device for generating a curvature of a vascular prosthesis 21. Its design is very similar to a known chain-stitch sewing machine with a lower support 28 with thread gripper 31 for material and with an arm 34 from which the needle movement is introduced.

In the device according to the invention, the fixed support 28 is enclosed by a support tube 23. With the aid of a feed device 27, which is connected to the support tube 23, said support tube 23 can execute axial movements. A feed drive 25 is provided for this purpose.

The arm 34 is no different from that of a commercially available chain-stitch sewing machine. The stroke of the sewing needle 35 is effected by a sewing needle drive 24 in a guide. A thread 33 is guided to the sewing needle 35 from a reel 32 arranged in proximity.

The support tube 23 is provided with an oblong hole 36 in an axial orientation in the wall, through which oblong hole 36 the sewing needle 35 can pass during the sewing procedure. The length of the oblong hole 36 corresponds to the maximum feed travel of the feed device.

The support tube 23 is used to receive the vascular prosthesis 21. The latter can be compressed manually on the support tube 23. For this purpose, one or two adjustable abutments for the vascular prosthesis 21 are provided on the support tube. It is also possible, however, to automate the procedure and to provide an abutment 30 which is driven by a motor (not shown in the figure) and which leads to uniform compression on each vascular prosthesis 21 to be worked.

It is often advantageous if the internal diameter of the vascular prosthesis 21 corresponds approximately to the external diameter of the support tube 23, preferably being only slightly smaller. In this way, a secure hold on the support tube 23 during the sewing procedure is ensured.

By means of the feed movement of the support tube 23, the compressed vascular prosthesis 21 can be provided with a seam 22 above the oblong hole 36. Arranged at the end of the support 28, inside the support tube 23, there is a thread gripper 31 which takes up the thread 33 inserted with the sewing needle 35 and chain-stitches it. As in known chain-stitch sewing machines, it is advantageous if the thread gripper 31 rotates and if the rotation is matched with the stroke of the needle. A gripper drive 26 is provided for this purpose.

Advantageously, the support tube 23 encloses the thread gripper 31 during the entire sewing procedure. The danger of gripping the rotating hook-shaped thread gripper 31 by hand is thus eliminated. The stiffness of the support tube 23 should be such that, during the sewing procedure, its cross-sectional shape is not changed, or is changed only inappreciably, on account of the radial load exerted by the sewing needle 35 on the pushed-on vascular prosthesis 21.

It has proven advantageous if the diameter of a rotating thread gripper 31 is not more than 3 mm smaller than the internal diameter of the support tube 23. Or, to express this the other way, the internal diameter of the support tube 23 needs to be only slightly greater than the diameter of the gripper, assuming sufficient stiffness of the material of the support tube. This is advantageous because the thread grippers 31 require a minimum diameter for reliable gripping and chain-stitching of the thread 33.

It should be noted that the scope of protection of the method is also intended to cover stabilization of an already thermally or chemically generated pre-curvature of a vascular prosthesis. Moreover, the method preferably covers the use of a vascular prosthesis that has a pleating. Such a vascular prosthesis can be particularly uniformly compacted or compressed.

The invention claimed is:

1. A textile vascular prosthesis comprising a pre-compressed vascular prosthesis, with a circulatory pleating formed by folds of the pleating lying on one another, and with an arch-shaped longitudinal flexion extending over at least a partial section and formed by asymmetric shortening gathering of the prosthesis wall by means of at least one longitudinal seam extending along the partial section,
   wherein the at least one longitudinal seam gathers the prosthesis wall while preserving the accordion-like structure and the compacted state of the pleating in the longitudinal direction,
   wherein the at least one longitudinal seam holds the vascular prosthesis in this state on the inside of the arch, and
   wherein in the area of the at least one longitudinal seam, the entire folds of the pleating lie tightly on one another without interstices.

2. The vascular prosthesis as claimed in claim 1, wherein the arch is preformed by thermal fixing.

3. The vascular prosthesis as claimed in claim 1, wherein the gathering is effected exclusively by the at least one longitudinal seam, with support by the thermal fixing.

4. The vascular prosthesis as claimed in claim 1, wherein the at least one longitudinal seam is formed from at least one continuous thread.

5. The vascular prosthesis as claimed in claim 1, wherein the at least one longitudinal seam is a machine seam.

6. The vascular prosthesis as claimed in claim 1, wherein the seam is formed from single chain stitches.

7. The vascular prosthesis as claimed in claim 1, wherein each seam is secured against undesired unravelling at the seam ends and, between the latter.

8. The vascular prosthesis as claimed in claim 1, further comprising several partial seams which extend one behind another in the longitudinal direction.

9. A curved vascular prosthesis according to claim 8, wherein between partial seams non-gathered sections of the prosthesis lie.

10. The vascular prosthesis as claimed in claim 1, wherein several longitudinal seams are formed from the same uninterrupted thread.

11. A curved vascular prosthesis according to claim 10, wherein several partial seams are formed from the same uninterrupted thread.

12. The vascular prosthesis as claimed in claim 1, wherein the at least one longitudinal seam is arranged in the area of the inside of the arch.

13. A curved vascular prosthesis according to claim 12, wherein all seams are arranged in the area of the inside of the arch.

* * * * *

UNITED STATES PATENT AND TRADEMARK OFFICE
CERTIFICATE OF CORRECTION

| | |
|---|---|
| PATENT NO. | : 8,128,683 B2 |
| APPLICATION NO. | : 11/632899 |
| DATED | : March 6, 2012 |
| INVENTOR(S) | : Lippoth et al. |

It is certified that error appears in the above-identified patent and that said Letters Patent is hereby corrected as shown below:

Title Page

(73) Assignees: should read     Aesculap AG, Tuttlingen/Donau (DE)
                                              Hans-Hinrich Sievers, Kronshagen (DE)

Signed and Sealed this
Fourteenth Day of August, 2012

David J. Kappos
*Director of the United States Patent and Trademark Office*